United States Patent [19]
Ulbrich et al.

[11] 3,937,733
[45] Feb. 10, 1976

[54] SALTS OF IODOMETHANESULFONIC ACID WITH ORGANIC BASES

[75] Inventors: Hermann Ulbrich; Wolfgang Beich, both of Berlin, Germany

[73] Assignee: Schering Aktiengesellschaft, Berlin & Bergkamen, Germany

[22] Filed: Mar. 31, 1972

[21] Appl. No.: 239,937

[30] Foreign Application Priority Data
Apr. 2, 1971  Germany............................ 2117014

[52] U.S. Cl.............. 260/501.19; 260/563 R; 424/5
[51] Int. Cl.²...................................... C07C 143/02
[58] Field of Search................................ 260/501.19

[56] References Cited
OTHER PUBLICATIONS
Stecher et al., The Merck Index (8th Ed.), Merck & Co., Inc. Rahway N.J. p. 674 (1968).

Hilal, Investigative Radiology, Vol. 5, pp. 458–468 (1970).

*Primary Examiner*—Joseph E. Evans
*Assistant Examiner*—G. Breitenstein
*Attorney, Agent, or Firm*—Millen, Raptes & White

[57] ABSTRACT

Salts of iodomethanesulfonic acid and an organic base, more particularly, glucamine, N-alkyl- and N,N-dialkylglucamines and N-hydroxyalkyl- and N,N-dihydroxyalkylglucamines, are useful as X-ray contrast agents, especially for spinal X-ray examination.

11 Claims, No Drawings

SALTS OF IODOMETHANESULFONIC ACID WITH ORGANIC BASES

BACKGROUND OF THE INVENTION

For the examination of the spinal canal, the sodium salt of monoiodomethanesulfonic acid (methiodal sodium) has been utilized for a long period of time. Compared to oily contrast media, this compound has the advantage of being rapidly and entirely resorbable. The very low viscosity of compositions comprising this compound makes it possible for the medium to penetrate into the finest fissures and thus render an excellent representation of the details in myelography. Disadvantages are the limited representation of the lumbar region and the necessity of prior spinal anesthesia, which constitutes a source of side reactions. According to SCHOBER (Radiopaque Agents and Liquor Space, Springer publishers 1964) a large number of the dangerous complications, such as conditions of shock and collapse, are ascribed to lumbar anesthesia.

It has now been found that the novel salts of this invention possess such a high compatibility with respect to the neural tissue that a lumbar anesthesia with its associated risks becomes superfluous. This essential advantage is attained without a reduction of the favorable properties of the known sodium salt, such as low viscosity and rapid resorption. Rather, the excellent compatibility of the novel salts permits readily a doubling of the commercially customary concentration of about 100 mg. of iodine per ml. of salt solution to 200 mg. of iodine per ml. of salt solution, whereby the image quality and thus the possibilities of evaluation of the myelographic examination are considerably increased.

SUMMARY OF THE INVENTION

The novel salts of this invention are those of monoiodomethanesulfonic acid with glucamine, N-alkyl- and N,N-dialkylglucamines. When the alkyl group contains more than one carbon atom, the latter two amines can be hydroxy substituted, i.e., N-hydroxyalkyl- and N,N-dihydroxyalkyl glucamines.

The alkyl portion of the glucamines generally contains not more than 4 carbon atoms, whether it be mono- or dialkyl.

This invention also relates to novel X-ray contrast agents comprising a novel salt of iodomethane sulfonic acid of this invention. In a method of use aspect, this invention relates to a method of X-ray examination, especially lumbar, comprising the administration of an effective amount of a novel X-ray contrast agent of this invention.

DETAILED DISCUSSION

Specific examples of the novel salts of iodomethanesulfonic acid of this invention include but are not limited to N-methylglucamine; N,N-dimethylglucamine; N-ethylglucamine; N-methyl,N-ethylglucamine; N,N-diethylglucamine; N-β-hydroxyethylglucamine; N-methyl,N-β-hydroxyethylglucamine and N,N-di-β-hydroxyethylglucamine.

Glucamine is a known amino sugar alcohol of the formula:

Glucamine and its N-mono- or N,N-disubstituted derivatives are obtained by reductive amination of glucose with the corresponding amines. Glucamine may also be obtained by reduction of glucose-oxime or by reductive cleavage of the N-N-bonding of glucose-hydrazone.

The novel salts are produced by neutralizing the iodomethanesulfonic acid with the selected organic base, up to a pH of 7, or by reacting a glucamine salt with alkali or alkaline earth iodomethanesulfonate.

This invention furthermore relates to novel X-ray contrast media comprising a novel salt of iodomethanesulfonic acid of this invention and their use in X-ray examination, especially spinal. The salts of this invention are formulated, in accordance with their preferred use as X-ray contrast media for myelography, into injectable aqueous solutions.

The novel X-ray contrast agents of this invention can be employed in the same manner as the known sodium salt of iodomethanesulfonic acid, preferably at a higher, e.g., double, the usual concentration. For example, a dose of 0.5 ml. of an X-ray contrast agent of this invention having an iodine content of 100 mg. per ml., administered to dogs lumbarly without local anesthesia, shows a good representation of the subdural fissures in the lumbal and thorax zones. However, a 2 ml. dose, with a content of 200 mg. of iodine per ml., affords a correspondingly excellent contrast effect and is tolerated without complications or serious side-effects. In any case, the salts can be administered to all mammals, in amounts effective to yield an X-ray contrast activity, the dosage range to humans being preferably equivalent to about 500 to 2000 mg. of iodine.

The novel compounds of this invention can be administered in the forms customarily employed in pharmaceuticals in admixture with a pharmaceutically acceptable carrier.

For parenteral administration, the soluble salts of this invention are preferably employed as an aqueous solution of a concentration preferably between about 30% by volume and about 80% by volume and preferably having a pH of about 5–7.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

N-Methylglucamine Salt of Iodomethanesulfonic Acid

An aqueous solution of sodium iodomethanesulfonate is passed through an ion exchange column in the H$^+$ form. The arrangement is protected from bright light, since the salt solution is somewhat sensitive to light. After a first run, the acidic main fraction is removed, neutralized with methylglucamine to a pH of 7, and thereafter concentrated to a content of 200 and/or 300 mg. of iodine/ml. Yield: 95% of theory. The solution can then be sterilized in accordance with Example 6.

When using dimethylglucamine or N-hydroxyethylglucamine in place of methylglucamine, the corresponding N,N-dimethylglucamine and N-hydroxyethylglucamine salts are obtained.

EXAMPLE 2

Glucamine Salt of Iodomethanesulfonic Acid

The acid is liberated from the sodium salt as described in Example 1. The solution of the acid is neutralized with glucamine to a pH of 7 and strongly concentrated under vacuum; by the addition of isopropanol, the glucamine salt precipitates in fine crystals. The salt is recrystallized from 95% ethanol. Melting point: 123°–124° C. Yield: 90% of theory.

EXAMPLE 3

N-Methylglucamine Salt of Iodomethanesulfonic Acid

The acid is liberated from the sodium salt as set forth in Example 1. The solution of the acid is neutralized with methylglucamine to a pH of 7, and the neutral solution is concentrated to syrupy consistency. By the addition of ethanol to the syrup, a crystalline product is obtained which is recrystallized from ethanol. Melting point: 93°–94° C. Yield: 91% of theory.

EXAMPLE 4

N,N-Dimethylglucamine Salt of Iodomethanesulfonic Acid

From free iodomethanesulfonic acid and N,N-dimethylglucamine, the N,N-dimethylglucamine salt of iodomethanesulfonic acid is obtained analogously to Example 3, m.p. 66°–67° C. (from ethanol). Yield: 87% of theory.

EXAMPLE 5

Glucamine Salt of Iodomethanesulfonic Acid

A hot solution of 14 g. of glucamine acetate in 100 ml. of methanol is stirred together with a warm solution of 12 g. of sodium iodomethanesulfonate in 120 ml. of methanol and concentrated under vacuum to 100 ml. After cooling, the thus-crystallized glucamine salt of iodomethanesulfonic acid is suction-filtered and washed with ethanol. Yield: 65% of theory. Melting point: 120°–123° C.

EXAMPLE 6

Preparation of a solution ready for use:

| | |
|---|---|
| Glucamine salt of iodomethanesulfonic acid | 635.00 g. |
| Calcium disodium salt of ethylenediamine-N,N'-tetraacetic acid | 0.11 g. |
| Sodium dihydrogen phosphate | 0.15 g. |
| Twice-distilled water | ad. 1000 ml. |

The glucamine salt solution is prepared in accordance with the above recipe, filled into ampoules or multivials and sterilized at 120° C. The solution contains 200 mg. of iodine per ml.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

Equivalent to the amines used for preparing the described salts are amino sugar alcohols with the amino function at a different position of the hexitol molecule, e.g. fructamin, galactamin etc.

What is claimed is:

1. A myelographic salt of iodomethanesulfonic acid with an amine selected from the group consisting of glucamine, N-alkylglucamine, N,N-dialkylglucamine and hydroxyalkylglucamines of the latter and former alkylglucamines containing more than one carbon atom in the alkyl radical, said amine in all cases having up to a total of four carbon atoms in the alkyl portion.

2. A salt of claim 1, wherein the amine is selected from the group consisting of N-methylglucamine; N,N-dimethylglucamine; N-ethylglucamine; N-methyl,N-ethylglucamine; N,N-diethylglucamine; N-$\beta$-hydroxyethylglucamine; N-methyl,N-$\beta$-hydroxyethylglucamine and N,N-di-$\beta$-hydroxyethylglucamine.

3. A salt of claim 1, wherein said amine is an N-alkylglucamine.

4. A salt of claim 1, wherein said amine is an N,N-dialkylglucamine.

5. A salt of claim 1, wherein said amine is an N-hydroxyalkylglucamine.

6. A salt of claim 1, wherein said amine is an N,N-dihydroxyalkylglucamine.

7. A salt of claim 1, selected from the group consisting of the N-methylglucamine salt of iodomethanesulfonic acid, the N,N-dimethylglucamine salt of iodomethanesulfonic acid, the N-hydroxyethylglucamine salt of iodomethanesulfonic acid and the glucamine salt of iodomethanesulfonic acid.

8. A salt of claim 7, the N-methylglucamine salt of iodomethanesulfonic acid.

9. A salt of claim 7, the N,N-dimethylglucamine salt of iodomethanesulfonic acid.

10. A salt of claim 7, the N-$\beta$-hydroxyethylglucamine salt of iodomethanesulfonic acid.

11. A salt of claim 7, the glucamine salt of iodomethanesulfonic acid.

* * * * *